(12) United States Patent
Taneja

(10) Patent No.: US 9,155,704 B1
(45) Date of Patent: Oct. 13, 2015

(54) MORE PALATABLE, BIOEQUIVALENT PHARMACEUTICAL COMPOSITION OF CARPROFEN

(71) Applicant: Jugal K. Taneja, Tampa, FL (US)

(72) Inventor: Jugal K. Taneja, Tampa, FL (US)

( * ) Notice: Subject to any disclaimer, the term of this patent is extended or adjusted under 35 U.S.C. 154(b) by 0 days.

(21) Appl. No.: 14/329,970

(22) Filed: Jul. 13, 2014

(51) Int. Cl.
*A61K 31/407* (2006.01)
*G01N 33/15* (2006.01)
*A61K 9/20* (2006.01)
*A61K 31/403* (2006.01)

(52) U.S. Cl.
CPC .............. *A61K 9/2004* (2013.01); *A61K 31/403* (2013.01); *A61K 31/407* (2013.01); *G01N 33/15* (2013.01)

(58) Field of Classification Search
CPC .............................. A61K 31/407; G01N 33/15
USPC ............................................. 514/411; 436/34
See application file for complete search history.

(56) References Cited

U.S. PATENT DOCUMENTS

| 6,541,025 B1 * | 4/2003 | Kershman | A61K 9/0056 424/439 |
| 2001/0002401 A1 * | 5/2001 | Evans | A61K 31/405 514/412 |
| 2003/0212123 A1 * | 11/2003 | DeMello | A61K 31/40 514/411 |

\* cited by examiner

*Primary Examiner* — Raymond Henley, III

(57) ABSTRACT

The present invention relates to a more palatable pharmaceutical composition comprising carprofen and at least one flavoring agent, and more particularly pertains to a more palatable and more voluntarily consumed pharmaceutically active dosage of carprofen, made available in the form of an orally administered tablet that is easy to swallow, with the same dissolution profile and bioequivalence of less palatable carprofen compositions, such as those compositions without a flavoring agent, and used for the indication of relieving clinical symptoms of pain and inflammation associated with osteoarthritis and postoperative surgery in mammals, by reduced prostaglandin production via inhibition of cyclooxygenase-2. Also included are analytical methods for in vitro dissolution testing of this unique composition to demonstrate bioequivalence to less palatable non-flavored and chewable compositions.

12 Claims, 1 Drawing Sheet

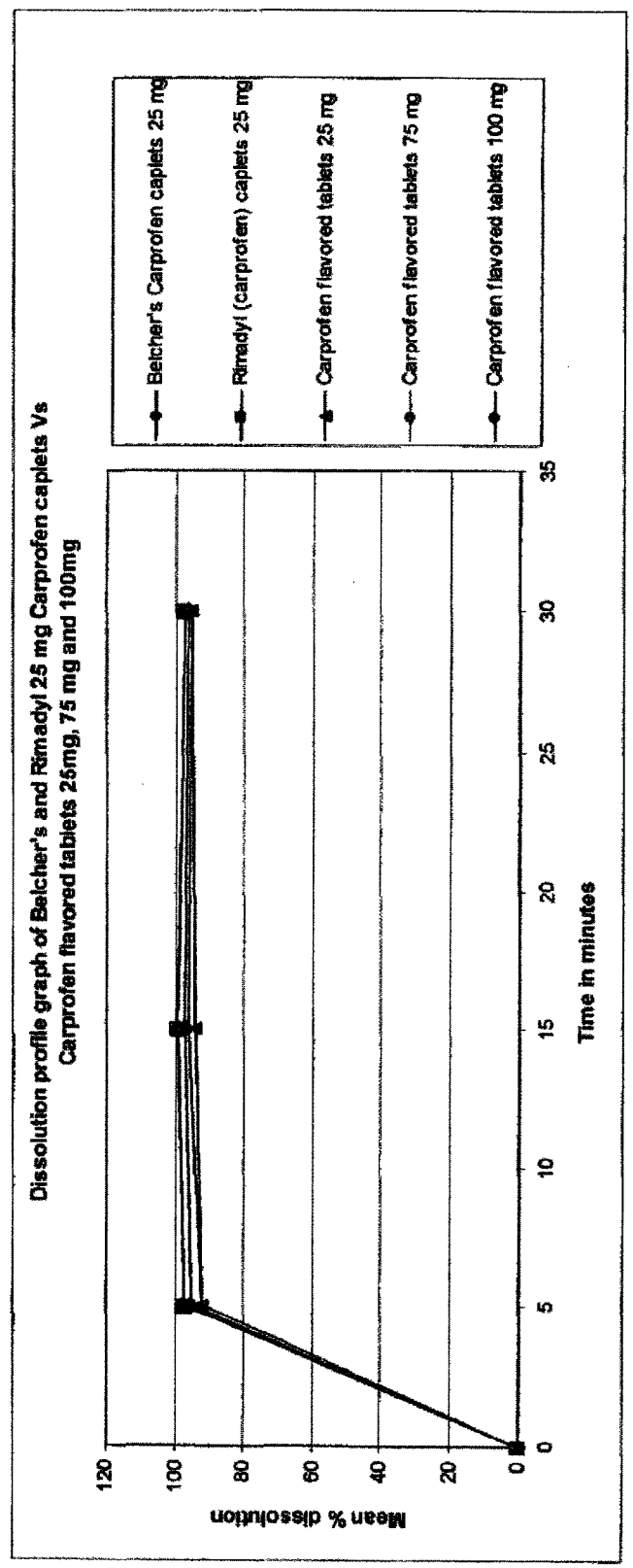

MORE PALATABLE, BIOEQUIVALENT PHARMACEUTICAL COMPOSITION OF CARPROFEN

FIELD OF THE INVENTION

The present invention relates to a more palatable pharmaceutical composition comprising carprofen and at least one flavoring agent, and more particularly pertains to a more palatable and more voluntarily consumed pharmaceutically active dosage of carprofen, made available in the form of an orally administered, non-chewable tablet that is easy to swallow, with similar dissolution profile and bioequivalence of less palatable carprofen compositions, such as those compositions without a flavoring agent, and used for the indication of relieving clinical symptoms of pain and inflammation associated with osteoarthritis and postoperative surgery in mammals, by reduced prostaglandin production via inhibition of cyclooxygenase-2. The present invention also includes novel analytical methods for in vitro dissolution testing of this unique composition to demonstrate bioequivalence to less palatable non-flavored and chewable compositions.

BACKGROUND OF THE INVENTION

Inflammation is a complex biomolecular cascade of events stimulated by cellular damage, whether the damage is caused by physical trauma, toxins, pathogens, or burns. Inflammation is the body's protective response to removing or blocking off such injurious stimuli, and beginning the process of wound healing and tissue repair. However, inflammation is often accompanied by painful soreness, swelling, heat and redness, which may also lead to loss of function.

In many cases, prolonged inflammation, called chronic inflammation, causes ongoing tissue destruction and healing at sites of inflammation. This is true of the debilitating autoimmune disease, rheumatoid arthritis, in which synovial joints become stiff and painful as joint surfaces slowly erode, which may decrease range of movement and lead to loss of function.

But inflammation can also occur around joints in patients suffering from osteoarthritis. Osteoarthritis is a painful degenerative disease associated with age and decreased proteoglycan content around joints, thereby, making joints less resilient and more susceptible to degradation. Furthermore, painful bone spurs may also form along these damaged, swollen joints. Although osteoarthritis is not an autoimmune disease, it can also be caused by inflammatory diseases.

Non-steroidal anti-inflammatory drugs (NSAIDs) are commonly used to reduce inflammation, along with their non-drowsy analgesic (pain relieving) and antipyretic (fever reducing) properties. Most NSAIDs serve as nonselective inhibitors of cyclooxygenase (COX), an enzyme that produces prostaglandins from arachidonic acid derived from the phospholipid bilayer of cellular membrane. Prostaglandins are the major signaling molecules involved in inflammation. Examples of NSAIDs include: acetaminophen, aspirin, ibuprofen, naproxen, and carprofen.

Carprofen is a selective cyclooxygenase-2 inhibitor that has been used in veterinarian medicine for decades to relieve postoperative pain, and to relieve chronic joint pain and inflammation associated with osteoarthritis, in dogs. Carprofen has the Chemical Abstracts Service (CAS) name of 6-Chloro-α-methyl-9H-carbazole-2-acetic acid and is a member of the carbazole family. Carbazoles have been synthesized as early as 1947, and their medicinal properties began to be studied shortly thereafter. Carprofen was first prepared in 1972 by Berger and Corraz of Hoffmann-La Roche Inc., as a useful anti-inflammatory and analgesic agent. Ulcer formation is a common side effect of many NSAIDs, especially if used often or in large dosages. Carprofen was believed to be advantageous over other NSAIDs because ulcer formation was rare. Hoffman La Roche began marketing carprofen as Imadyl in the early 1980s and this product was eventually sold to Pfizer for use in veterinary medicine as a chewable form, called Rimadyl, for dogs in the mid-1990s. However, non-chewable tablets of carprofen have been sold as a generic drug for many years.

The success of Pfizer's Rimadyl chewable tablet is likely attributed to better dog owner and dog compliance because of greater palatability over generic brands. Palatability is especially important for good dosing compliance in veterinary medicine with regards to owner administered oral tablets. Likewise, brands with reduced palatability can lead to poor owner and patient compliance, which often leads to missed doses or increased lag time between doses. Without good palatability, owners may try placing or crushing an oral tablet in food. Even so, the challenges faced by owners administering a non-palatable tablet to a reluctant animal can be frustrating when long-term dosing is required, such as for chronic illnesses, and can lead to noncompliance and poor clinical outcomes. So although different brands of a drug product, such as carprofen, are shown clinically to have equivalent safety and efficacy, i.e. bioequivalence, differences in palatability and compliance often remain.

The ideal oral tablet for veterinary medicine should be palatable and consumed voluntarily with an at least 90% voluntary acceptance rate. Palatability may be achieved by masking the foul taste of active pharmaceutical ingredients and/or by adding food based products or other flavors. Factors affecting palatability include taste, odor, appearance, and texture. However, the addition of flavoring agents generally change the dissolution profile of the drug and its bioequivalence. Yet, there remains a need to produce a more palatable and more voluntarily consumed orally administered tablet composition of carprofen that is easy to swallow, and has the same dissolution profile and bioequivalence of less palatable carprofen compositions, so that it can also be manufactured with greater ease and less cost than the available "chewable" tablet of carprofen (e.g., Rimadyl). As such, the preferred composition described herein is manufactured using the process of dry blending and tablet compression, and avoids the use of coatings; which require solvents, polymers and/or plasticizers, along with detackifiers, defoamers, surfactants; that can add much time and cost to the manufacturing process and can lead to problems of uniformity among tablets.

DESCRIPTION OF THE PRIOR ART

Methods of preparing and administering compositions of anti-inflammatory agents, such as NSAIDs, to treat a myriad of illnesses is known in the prior art.

By way of example, U.S. Pat. No. 3,896,145 by Berger and Corraz of Hoffmann-La Roche Inc. describes the preparation of carbazoles, including carprofen, that serve as useful anti-inflammatory and analgesic agents.

U.S. Pat. No. 4,871,733 describes the use of NSAIDs, such as carprofen, for treating cold and cough symptoms.

U.S. Pat. No. 6,506,785 assigned to Pfizer describes a new indication for carprofen for preventing the early stages of degeneration of articular cartilage or subchondral bone in mammals without clinical symptoms. Therefore, U.S. Pat. No. 6,506,785 assigned to Pfizer is limited to treating mammals prior to the onset of clinical symptoms associated with the degeneration of articular cartilage or subchondral bone. As such, U.S. Pat. No. 6,506,785 describes a battery of invasive biochemical tests, along with expensive radiographic and magnetic resonance imaging, to determine if mammals are in the early stages of this disease. The method of this patent also fails to describe making a chondroprotective compound more palatable to enhance user compliance and voluntary acceptance.

U.S. Pat. Appl. No. 20040166157 assigned to Pfizer describes numerous different palatable chewable controlled-release formulations for companion animals; one of which includes carprofen, but is very limited to using a coating of polymeric ethylcellulose or an acrylic polymer that is an anionic copolymer made from methacrylic acid and methacrylate. This patent application is also limited by its range of average particle size of the pharmaceutically active agent, along with the percent by weight range of its coating and palatability improving agent. Moreover, the use of coatings require solvents, polymers and/or plasticizers, along with detackifiers, defoamers, and surfactants that can add much time and cost to the manufacturing process and can lead to problems of uniformity among tablets.

U.S. Pat. Appl. No. 20030212123 and International Appl. No. WO/1998/050033 assigned to Pfizer describe a method of treating or preventing pain and inflammatory processes and diseases associated with the activity of inducible cyclooxygenase-2 in dogs while reducing the undesirable side effects of cyclooxygenase-1, whereby the patent is limited to a selectivity ratio of COX-2:COX-1 activity inhibition being at least 3:1 based on ex vivo testing of inhibition levels in whole blood measured at a dose giving greater than or equal to 80% COX-2 inhibition. Such a method may be appreciated for novel derivatives of carprofen, but seems redundant for carprofen which has been used for similar reasons for decades in the prior art. Furthermore, this application also describes a composition for an oral controlled release dosage form of carprofen that is administered in large dosage to maintain plasma carprofen levels above 10 microg/mL for a period of time greater than 10.5 hours; the carprofen being selective for cyclooxygenase-2; for treating pain and inflammation, without any specific indications. Namely, this application fails to claim the use of this method for the indications of arthritis and postoperative pain. Furthermore, this application is vague as to the preferred dosage form, e.g. solid, chewable, liquid, or injectable; and is vague as to the preferred combination of multiple pharmaceutically active ingredients. Most foreign filings of this international application were refused or rejected, as seen by this application's national phase.

U.S. Pat. Appl. No. 20010012849 describes the use of administering enantiomerically pure R-NSAID, such as R-carprofen, of at least 200 milligrams, or of at least 2.5 milligrams per kilogram of animal's body weight, for treating inflammation. However, the R-carprofen enantiomeric form has much less cyclooxygenase inhibiting activity than the S-carprofen enantiomeric form, and may be ineffective in treating inflammation.

U.S. Pat. No. 6,497,899 describes non-friable, rapidly disintegrating, fast-dissolving solid dosage forms that are produced from pharmaceutically acceptable steam extruded polymers. The solid dosage forms dissolve in the mouth and are particularly useful for subjects that require or desire oral medication, but have difficulty swallowing standard oral dosage forms such as tablets, or in subjects suffering from emesis.

It is the goal of the current invention to provide an improved pharmaceutical composition of a more palatable and more voluntarily consumed orally administered tablet form of carprofen that is easy to swallow, and has the same dissolution profile and bioequivalence of less palatable carprofen compositions.

It is another goal of the current invention to provide an improved pharmaceutical composition of a more palatable and more voluntarily consumed orally administered tablet composition of carprofen that does not require coating and is easier to manufacture, and is also susceptible of a lower cost of manufacture with regard to machinery, materials, and labor, than the available "chewable" tablet of carprofen (Rimadyl).

Before explaining at least one embodiment of the invention in detail, it is to be understood that the invention is not limited in its application to the details of preparation set forth in the following description. The invention is capable of other embodiments and of being practiced and carried out in various other ways. Also, it is to be understood that the phraseology and terminology employed herein are for the purpose of descriptions and should not be regarded as limiting.

DETAILED DESCRIPTION OF THE FIGURE

FIG. 1 is a graphic representation of the results of an in vitro dissolution experiment conducted according to the Applicant's analytical method comprising the dissolving of at least one oral pharmaceutical formulation of carprofen in at least one Peak vessel/Peak flask. In this in vitro dissolution experiment, a novel carprofen, flavored, non-chewable tablets according to this invention (25 mg, 75 mg, and 100 mg) was tested along with a generic brand of non-flavored carprofen 25 mg caplets and Rimadyl brand 25 mg caplets. Each different tablet or caplet was tested twelve times. Time in minutes is shown on the horizontal axis, and mean percent dissolution, based on ultraviolet spectrophotometric absorbance at 300 nm, is shown on the vertical axis.

DETAILED DESCRIPTION OF THE INVENTION

The present invention relates to a more palatable pharmaceutical composition comprising carprofen and at least one flavoring agent, and more particularly pertains to a more palatable and more voluntarily consumed pharmaceutically active dosage of carprofen, made available in the form of an orally administered tablet that is easy to swallow, with similar dissolution profile and bioequivalence of less palatable carprofen compositions, with the indication of relieving pain and inflammation associated with osteoarthritis and postoperative surgery in mammals, by inhibition of cyclooxygenase-2.

To produce this more palatable and more voluntarily consumed pharmaceutically active dosage of carprofen, at least one suitable flavoring agent, pleasing to canines, replaces at least some filler, and unexpectedly, without changing the dissolution profile and bioequivalence of the composition. The preferred embodiment of this invention utilizes artificial powdered beef flavor (PC-0125), manufactured by Pharma Chemie, Syracuse, Nebr., USA, which has a roast beef and liver flavor and odor; itself comprising not less than 25% w/w protein, not less than 2% w/w fat, and between 3% and 7% moisture. The said artificial beef flavoring preferably replaces at least some amount of at least one filler, preferably microcrystalline cellulose, such that this flavoring agent comprises 5% w/w of the carprofen tablet.

The preferred embodiment of this invention has the following composition: carprofen, 13.97% w/w; microcrystalline cellulose, NF (Avicel PH-101), 72.00% w/w; croscarmellose sodium, NF (Solutab, Type A), 4.97% w/w; FD&C Yellow #6/sunset yellow FCF AL 15-18% (5285), 0.08% w/w; artificial powdered beef flavor (PC-0125), 5.00% w/w; purified stearic acid, NF (Hystrene 9718), 1.99% w/w; and magnesium stearate, NF, 1.99% w/w. [An example of a less palatable tablet composition may have 0% w/w beef flavoring and 77.00% w/w microcrystalline cellulose, with other components being the same]. The dosage of carprofen in this composition is preferably 100 mg/tablet, 75 mg/tablet, or 25 mg/tablet.

For example, a 100 mg carprofen tablet of the preferred embodiment would consist of 100 mg of carprofen; 515.52 mg of microcrystalline cellulose, 35.56 mg of croscarmellose sodium; 0.56 mg of FD&C Yellow #6/sunset yellow FCF, 35.80 mg of artificial powdered beef flavor (PC-0125), 14.28 mg of purified stearic acid; and 14.28 mg of magnesium stearate.

In this preferred embodiment, carprofen is the only pharmaceutically active ingredient, and all other ingredients are excipients. The microcrystalline cellulose serves as a binder and a filler. The croscarmellose sodium, which is an internally cross-linked sodium caboxymethylcellulose, is used as a disintegrant agent, that expands and dissolves when wetted by digestive fluids to make carprofen available for absorption after being swallowed. The FD&C Yellow #6 is used as a coloring agent. The magnesium stearate and stearic acid are added as lubricants that make the process of tablet punching more efficient.

This composition is preferably prepared quickly and easily by a dry method of tablet preparation, one that avoids unnecessary solvents, heat drying, and troublesome tablet coating procedures, which may sometimes lead to problems in stability and uniformity. This dry method of tablet preparation, therefore, is performed by dry blending ingredients, some of which are pre-sifted, and by tablet compression using a tablet press. The resulting finished product specification for carprofen tablets produced by this method is stable and complies with ICH Q3B impurities specifications and ICH Q3C residual solvents requirements.

Other embodiments of this invention may include any number of other excipients and/or % w/w of these excipients; such as antiadherents, binders, disintegrants, fillers, diluents, colors, lubricants, glidants, preservatives, sorbents, sweeteners, etc.; which may substitute for some or all of the excipients listed in the primary embodiment of the invention, such as long as at least one excipient is a flavoring agent that makes the tablet more palatable, and that the dissolution profile and bioequivalence of the dosage form remains nearly the same. As such, one skilled in the art can conceive of other embodiments of this invention that do not depart from the scope of this application and, therefore, the primary embodiment of this invention should not be regarded as limiting.

The invention disclosed is a pharmaceutical composition of a more palatable tablet comprising the pharmaceutically active ingredient carprofen and at least two excipients, whereby the amount of carprofen is about 13.97% of the total weight of said palatable tablet. At least one excipient of said at least two excipients comprises at least one flavoring agent preferably having a meat-like taste and odor. The least one flavoring agent may also optionally comprise a sweetener. The at least one flavoring agent is able to at least partially mask the taste of said pharmaceutically active ingredient carprofen. The tablet is structured to contain a combined weight of one or more flavoring agents of no more than about 5% of the total weight of said palatable tablet. The palatable tablet further has an in vitro dissolution profile specifically determined by use of a Peak vessel/Peak flask during in vitro dissolution testing as part of a novel analytical method. This analytical method developed for this palatable tablet, disclosed herein, provides an in vitro dissolution profile and bioequivalence nearly identical to less palatable carprofen tablet compositions, including compositions not containing a flavoring agent.

The palatable tablet of the invention is further structured to be preferably non-coated. The tablet is non-chewable, and is further structured to be easily swallowed for oral administration without chewing. The palatability of the tablet through the use of its flavoring agents and unique structure permits the tablet to have an at least 90% voluntary acceptance rate when consumed voluntarily by a veterinary animal. When swallowed by the oral route, the palatable table is able to relieve clinical symptoms of pain and inflammation associated with osteoarthritis and postoperative veterinary surgery in mammals, including canines, by inhibiting prostaglandin formation by inhibiting cyclooxygenase-2.

The palatable tablet of the invention preferably includes filler excipients, such as microcrystalline cellulose, disintegrant excipients to ensure proper bioavailability, such as croscarmellose sodium, coloring agents, such as FD&C Yellow #6/sunset yellow FCF AL 15-18%, and lubricant excipients, such as purified stearic acid and/or magnesium stearate.

The said palatable tablet preferably contains filler excipient(s) with a combined weight of 72.00% of the total weight of said palatable tablet; disintegrant excipient(s) with a combined weight of 4.97% of the total weight of said palatable tablet, coloring agent excipient(s) with a combined weight of 0.08% of the total weight of said palatable tablet, and lubricant excipient(s) with a combined weight of 3.98% of the total weight of said palatable tablet.

To formulate the disclosed invention of a pharmaceutical composition of a palatable tablet comprising the pharmaceutically active ingredient carprofen, and to ensure its bioavailability and bioequivalence upon ingestion, a novel analytical method was developed. This analytical method includes dissolving at least one oral pharmaceutical formulation of carprofen in at least one Peak vessel/Peak flask during at least one in vitro dissolution test. This analytical method was tested with the palatable carprofen tablet disclosed by this invention; and tested against less palatable carprofen tablet compositions, including compositions not containing a flavoring agent, and instead, containing a greater amount of filler excipients. This unique method provided a novel way to demonstrate bioequivalence between meat flavored and unflavored carprofen solid oral compositions.

A description of this method and experimental results follow. Peak vessels were used for the experiment with two identical dissolutions apparatus (United States Pharmacopeia [USP] apparatus II). A Peak vessel is a flask or beaker with a bottom wall surface including a cone shape having a tip pointing upwards into the interior of the vessel. It was unexpectedly found that a Peak vessel could provide unique fluid dynamics to the mixing of this novel flavored carprofen formulation to enhance release rates and prevent clumping of disintegrated mass at the bottom of a mixing apparatus. An in vitro dissolution experiment was conducted, which tested the novel carprofen, flavored, non-chewable tablets of this invention (25 mg, 75 mg, and 100 mg), according to the preferred embodiment, in comparison to a generic brand of non-flavored carprofen 25 mg caplets and Rimadyl brand 25 mg caplets. In this experiment, the dissolution medium consisted of USP simulated intestinal fluid without enzymes, pH 7.5. The dissolution testing of samples was performed in the Peak vessel with a paddle speed of 50 rotations per minute for 30 minutes, with samples collected at three time intervals (5, 15 and 30 minutes). Each different tablet or caplet was tested twelve times. Carprofen content of the novel flavored tablet samples, Belcher's generic carprofen caplets, and Rimadyl (carprofen) caplet samples were determined by measuring ultraviolet spectrophotometric absorbance at 300 nm based on the USP monograph method with reference carprofen materials. The percent of drug released from each dose strength for each formulation was calculated at each time point. A graphic representation of these results with time in minutes on the horizontal axis, and mean percent dissolution on the vertical axis, is shown in FIG. 1.

FIG. 1 reveals the nearly equivalent dissolution profiles of novel, non-chewable, carprofen flavored tablets 25 mg, 75 mg, and 100 mg, according to the preferred embodiment of this invention (designated by triangle, circle, and oval in the graph, respectively), in comparison to the dissolution profiles of a generic brand of non-flavored carprofen 25 mg caplets (designated by diamond in the graph) and Rimadyl brand carprofen 25 mg caplets (designated by square in the graph); using the novel analytical method with Peak vessel disclosed in this application. In each sample tested, more than 85% dissolution occurred within 15 minutes. In fact, greater than 90% dissolution is achieved within 5 minutes with this method. Such unexpected in vitro results relate to the bioequivalence among the novel flavored, non-chewable, tablet composition of this invention compared to less palatable compositions of carprofen of the prior art.

DEFINITIONS

The term "pharmaceutical" is understood in the context of the present invention to mean relating to pharmacy or to pharmaceutics, of or relating to drugs used in medical treatment.

The term "composition" as used herein, can be interchangeable with the term pharmaceutical "formulation," the list of physiologically "active" pharmaceutical ingredients and non-active ingredients ("excipients").

The term "oral administration" generally includes buccal, sublabial and sublingual administration, as well as enteral administration. In the context of this application, oral administration generally means administered to the mouth and swallowed.

The term "burn" is a type of tissue injury caused by heat, electricity, chemicals, radiation, and friction.

The term "palatability" refers to the level of voluntary acceptance and ingestion of a product.

The term "enantiomers" describe stereoisomers, having non-superposable mirror images, and having the property of rotating plane-polarized light by equal amounts in opposite directions.

The terms "uniform" and "uniformity," as they apply to "dosage uniformity," relate to the homogeneity of: composition, shape, size, surface texture, and form among different doses and among different batches of product.

The term "disintegrable" describes the property of being able to disintegrate or fragment.

The term "indication," as it relates to drug indication, refers to reasons for prescribing a drug, such as may be for the proper treatment of a disease, which may be necessitated by its cause or symptoms.

The terms "dissolution" and "dissolution profile," as they relate to pharmaceutical compositions, describe disintegration and solubilization rates (release rates) of a drug, as a characteristic of that drug in a specific formulation.

The term "bioequivalence" describes the absence of a significant difference in the rate and extent to which the active ingredient in different pharmaceutical formulations becomes available at the site of drug action when administered at the same molar dose and under similar conditions. The results of bioequivalence studies are assessed by the FDA.

Other variations and embodiments of the invention described herein will now be apparent to those of skill in the art without departing from the disclosure of the invention or the coverage of the claims to follow.

What is claimed is:

1. A pharmaceutical composition of a palatable tablet comprising the pharmaceutically active ingredient carprofen and at least two excipients, whereby the amount of carprofen is about 13.97% of the total weight of said palatable tablet, and whereby at least one excipient of said at least two excipients comprises at least one flavoring agent;
    said at least one flavoring agent having a meat-like taste;
    said at least one flavoring agent having a meat-like odor;
    said at least one flavoring agent further able to at least partially mask the taste of said pharmaceutically active ingredient carprofen;
    said palatable tablet structured to contain a combined weight of one or more flavoring agents of no more than about 5% of the total weight of said palatable tablet;
    said palatable tablet further having an in vitro dissolution profile specifically determined by use of a Peak vessel/Peak flask during in vitro dissolution testing as part of an analytical method;
    said palatable tablet further having an in vitro dissolution profile and bioequivalence nearly identical to less palatable carprofen tablet or caplet compositions, including compositions not containing a flavoring agent;
    said palatable tablet further structured to be non-coated;
    said palatable tablet further being deliverable by oral administration;
    said palatable table further being structured to be non-chewable;
    said palatable tablet further structured to be easily swallowed for oral administration without chewing;
    said palatable tablet associated with an at least a 90% voluntary acceptance rate when consumed voluntarily;
    said palatable tablet further being able to relieve clinical symptoms of pain and inflammation associated with osteoarthritis and postoperative veterinary surgery in mammals, including canines, when swallowed, by inhibiting prostaglandin formation by inhibiting cyclooxygenase-2;
    said palatable tablet further comprising filler excipient(s) with a combined weight of 72.00% of the total weight of said palatable tablet; disintegrant excipient(s) with a combined weight of 4.97% of the total weight of said palatable tablet, coloring agent excipient(s) with a combined weight of 0.08% of the total weight of said palatable tablet, and lubricant excipient(s) with a combined weight of 3.98% of the total weight of said palatable tablet.

2. The pharmaceutical composition the palatable tablet of claim 1, whereby said filler excipient(s) is at least comprising microcrystalline cellulose.

3. The pharmaceutical composition the palatable tablet of claim 1, whereby said disintegrant excipient(s) is at least comprising croscarmellose sodium.

4. The pharmaceutical composition the palatable tablet of claim 1, whereby said coloring agent excipient(s) is at least comprising FD&C Yellow #6/sunset yellow FCF AL 15-18%.

5. The pharmaceutical composition the palatable tablet of claim 1, whereby said lubricant excipient(s) is at least comprising purified stearic acid and/or magnesium stearate.

6. The pharmaceutical composition the palatable tablet of claim 1, whereby said at least one flavoring agent is at least comprising artificial powdered beef flavor (PC-0125).

7. The pharmaceutical composition the palatable tablet of claim 1, whereby said palatable tablet further includes a sweetener.

8. A pharmaceutical composition of a palatable tablet comprising the pharmaceutically active ingredient carprofen and at least two excipients, whereby the amount of carprofen is about 13.97% of the total weight of said palatable tablet, and whereby at least one excipient of said at least two excipients comprises at least one flavoring agent;
   said at least one flavoring agent preferably having a meat-like taste;
   said at least one flavoring agent preferably having a meat-like odor;
   said at least one flavoring agent optionally comprising a sweetener;
   said at least one flavoring agent further able to at least partially mask the taste of said pharmaceutically active ingredient carprofen;
   said palatable tablet structured to contain a combined weight of one or more flavoring agents of no more than about 5% of the total weight of said palatable tablet;
   said palatable tablet further having an in vitro dissolution profile specifically determined by use of a Peak vessel/Peak flask during in vitro dissolution testing as part of an analytical method;
   said palatable tablet further having an in vitro dissolution profile and bioequivalence nearly identical to less palatable carprofen tablet or caplet compositions, including compositions not containing a flavoring agent;
   said palatable tablet further structured to be preferably non-coated;
   said palatable tablet further being deliverable by oral administration;
   said palatable table further being structured to be non-chewable;
   said palatable tablet further structured to be easily swallowed for oral administration without chewing;
   said palatable tablet associated with an at least a 90% voluntary acceptance rate when consumed voluntarily;
   said palatable tablet further being able to relieve clinical symptoms of pain and inflammation associated with osteoarthritis and postoperative veterinary surgery in mammals, including canines, when swallowed, by inhibiting prostaglandin formation by inhibiting cyclooxygenase-2.

9. A pharmaceutical composition of a palatable tablet comprising the pharmaceutically active ingredient carprofen and at least two excipients, whereby the amount of carprofen is about 13.97% of the total weight of said palatable tablet, and whereby at least one excipient of said at least two excipients comprises at least one flavoring agent having a meat-like taste and comprising artificial powdered beef flavor, and preferably PC-0125, in an amount no more than about 5% of the total weight of said palatable tablet;
   said at least one flavoring agent further able to at least partially mask the taste of said pharmaceutically active ingredient carprofen;
   said palatable tablet further having an in vitro dissolution profile specifically determined by use of a Peak vessel/Peak flask during in vitro dissolution testing as part of an analytical method;
   said palatable tablet further having an in vitro dissolution profile and bioequivalence nearly identical to less palatable carprofen tablet or caplet compositions, including compositions not containing a flavoring agent;
   said palatable tablet further structured to be non-coated;
   said palatable tablet further being deliverable by oral administration;
   said palatable table further being structured to be non-chewable;
   said palatable tablet further structured to be easily swallowed for oral administration without chewing;
   said palatable tablet associated with an at least a 90% voluntary acceptance rate when consumed voluntarily;
   said palatable tablet further being able to relieve clinical symptoms of pain and inflammation associated with osteoarthritis and postoperative veterinary surgery in mammals, including canines, when swallowed, by inhibiting prostaglandin formation by inhibiting cyclooxygenase-2;
   said palatable tablet further comprising microcrystalline cellulose with a weight of 72.00% of the total weight of said palatable tablet; croscarmellose sodium with a weight of 4.97% of the total weight of said palatable tablet, FD&C Yellow #6/sunset yellow FCF AL 15-18% with a weight of 0.08% of the total weight of said palatable tablet, and purified stearic acid with a weight of 1.99% of the total weight of said palatable tablet, and magnesium stearate with a weight of 1.99% of the total weight of said palatable tablet.

10. An analytical method comprising the dissolving of at least one oral pharmaceutical formulation of carprofen in at least one Peak vessel/Peak flask during at least one in vitro dissolution test.

11. An analytical method comprising the dissolving of at least one oral pharmaceutical formulation of carprofen in at least one Peak vessel/Peak flask during at least one in vitro dissolution test, said at least one oral pharmaceutical formulation of carprofen including a pharmaceutical composition of a palatable tablet comprising the pharmaceutically active ingredient carprofen and at least two excipients whereby at least one excipient of said at least two excipients comprises at least one flavoring agent.

12. A method for preparing and testing a pharmaceutical composition of a palatable tablet comprising the pharmaceutically active ingredient carprofen and at least two excipients, whereby the amount of carprofen is about 13.97% of the total weight of said palatable tablet, and whereby at least one excipient of said at least two excipients comprises at least one flavoring agent;
   said at least one flavoring agent preferably having a meat-like taste;
   said at least one flavoring agent preferably having a meat-like odor;
   said at least one flavoring agent optionally comprising a sweetener;
   said at least one flavoring agent further able to at least partially mask the taste of said pharmaceutically active ingredient carprofen;
   said palatable tablet structured to contain a combined weight of one or more flavoring agents of no more than about 5% of the total weight of said palatable tablet;
   said palatable tablet further having an in vitro dissolution profile specifically determined by use of a Peak vessel/Peak flask during in vitro dissolution testing as part of an analytical method;
   said palatable tablet further having an in vitro dissolution profile and bioequivalence nearly identical to less palatable carprofen tablet or caplet compositions, including compositions not containing a flavoring agent;

said palatable tablet further structured to be preferably non-coated;
said palatable tablet further being deliverable by oral administration;
said palatable table further being structured to be non-chewable;
said palatable tablet further structured to be easily swallowed for oral administration without chewing;
said palatable tablet associated with an at least a 90% voluntary acceptance rate when consumed voluntarily;
said palatable tablet further being able to relieve clinical symptoms of pain and inflammation associated with osteoarthritis and postoperative veterinary surgery in mammals, including canines, when swallowed, by inhibiting prostaglandin formation by inhibiting cyclooxygenase-2.

* * * * *